(12) United States Patent
Odermatt et al.

(10) Patent No.: US 8,498,744 B2
(45) Date of Patent: Jul. 30, 2013

(54) SURGICAL ROBOTIC SYSTEMS WITH MANUAL AND HAPTIC AND/OR ACTIVE CONTROL MODES

(75) Inventors: Daniel Odermatt, Fort Lauderdale, FL (US); Renen Bassik, Miami, FL (US); Chunyan Wu, Parkland, FL (US); Danielle Landeck, Delray Beach, FL (US); Jason Wojcik, Weston, FL (US)

(73) Assignee: Mako Surgical Corporation, Fort Lauderdale, FL (US)

( * ) Notice: Subject to any disclaimer, the term of this patent is extended or adjusted under 35 U.S.C. 154(b) by 127 days.

(21) Appl. No.: 13/174,051

(22) Filed: Jun. 30, 2011

(65) Prior Publication Data

US 2013/0006267 A1    Jan. 3, 2013

(51) Int. Cl.
*G06F 19/00* (2011.01)
(52) U.S. Cl.
USPC ........... 700/245; 700/248; 700/258; 700/260; 701/93; 701/469; 701/472; 340/466; 340/905; 180/65.21; 180/170; 318/568.1

(58) Field of Classification Search
USPC ................... 701/93, 469, 472; 700/245, 248, 700/258, 260; 340/466, 905; 180/65.21, 170; 318/568.1
See application file for complete search history.

(56) References Cited

U.S. PATENT DOCUMENTS

| | | | | |
|---|---|---|---|---|
| 5,408,409 | A * | 4/1995 | Glassman et al. | 600/407 |
| 5,820,623 | A * | 10/1998 | Ng | 606/1 |
| 7,239,940 | B2 * | 7/2007 | Wang et al. | 700/245 |
| 8,005,571 | B2 * | 8/2011 | Sutherland et al. | 700/248 |
| 8,095,200 | B2 * | 1/2012 | Quaid, III | 600/407 |

* cited by examiner

*Primary Examiner* — James Trammell
*Assistant Examiner* — McDieunel Marc
(74) *Attorney, Agent, or Firm* — Miller, Matthias & Hull LLP

(57) ABSTRACT

A surgical robotic system is disclosed that provides a combination of a programmed control, when a high degree of accuracy is required and manual control when a high degree of accuracy is not required.

25 Claims, 4 Drawing Sheets

SURGICAL ROBOTIC SYSTEMS WITH MANUAL AND HAPTIC AND/OR ACTIVE CONTROL MODES

TECHNICAL FIELD

This disclosure relates generally to surgical robotic systems for modifying bone or rigid tissue. More specifically, this disclosure relates to surgical robotic systems that include multiple control modes, such as an active control mode and/or a passive control mode, as well as a manual control mode, which provides the surgeon with more freedom than the active or passive control modes alone.

BACKGROUND AND DESCRIPTION OF THE RELATED ART

Robotic systems are often used in applications that require a high degree of accuracy and/or precision, such as surgical procedures or other complex tasks. A surgical robot typically includes one or more robotic arms coupled to a surgical cutting tool. The arm is linked to a controller and a navigation or tracking system. Surgical robotic systems may include various types of robots and various types of control schemes including "autonomous" surgical robotic systems with actively constrained autonomous control and "interactive" surgical robotic systems with passively constrained haptic control. Actively and passively controlled surgical robotic systems may be used in many surgical fields, including various orthopedic and non-orthopedic procedures.

Actively controlled surgical robots essentially take the cutting tools out of the hands of the surgeon's hand, and instead, execute a procedure according to a predetermined plan that has been programmed into the memory of the controller. On the other hand, a passively controlled robotic arm provides the surgeon with the ability to direct the robot arm as desired within certain limitations. One form of a passive system is a haptically controlled robotic arm that provides the surgeon with tactile feedback as the tool engages the patient's anatomy or if the tool engages or begins to cross a predetermined virtual boundary. One goal of a haptically controlled surgical robotic system is to augment a surgeon's sensory feedback during a procedure, while preventing the surgical tool from crossing the virtual boundary that may be in the form of a predefined haptic path or geometric haptic volume.

Both actively controlled and passively controlled surgical robots are used for procedures that require a high degree of accuracy. For example, referring to FIGS. 1-3, in hip replacement surgery, a surgeon can use an actively or passively guided robotic arm 20 equipped with a semi-spherical reamer 23 to sculpt a semi-spherical indentation in the acetabulum 21, which is a cup-shaped socket in the pelvis 22. The acetabulum 21 receives a cup commonly referred to as an acetabular cup (not shown) that, in turn receives a resurfaced femoral head in a partial hip arthroplasty or, in the case of a total hip arthroplasty (THA), a ball portion of a hip implant.

In an actively controlled system, after an initial incision is made, the surgeon manipulates the robotic arm 20 to move a cutting tool or reamer 23 that is coupled to the robotic arm 20 into position near the acetabulum 21. Then, the active controls of the system take over and the robotic arm 20 and reamer 23 follow a predetermined course until the desired indention in the acetabulum 21 is completed.

In contrast, a passively constrained haptic system provides the surgeon with some, but limited control over the cutting tool. Specifically, under haptic control, the surgeon guides the robotic arm 20 and reamer 23 during the formation of the indentation in the acetabulum. As long as the surgeon maintains the cutting tool within predefined virtual cutting boundary that is typically defined by a straight line haptic path or geometric haptic volume, the surgeon can move the robotic arm with low friction and low inertia. However, the robotic arm provides haptic (or force) feedback that prevents the surgeon from moving the cutting tool beyond the virtual cutting boundary. Further, to avoid inaccurate placement of the acetabular cup, unintended reaming of healthy bone and/or inaccurate bone preparation, if the center of the reamer 23 is not maintained along the haptic path or within the haptic volume of the virtual cutting boundary, some controllers may not allow the reamer 23 to operate.

The above-described actively and passively controlled robotic systems, though useful for THAs and many other procedures, may not be optimally suited for related procedures that do not require a high degree of accuracy. For example, surgeons frequently remove osteophytes and irregular bone, as well as labrum and other soft tissue around the rim of the acetabulum to provide the access required for reaming the acetabulum accurately. Further, additional manual resection may be necessary while fitting the acetabular cup in the reamed acetabulum and afterwards, especially if some bone or tissue irregularities are created during the reaming and fitting of the cup.

In contrast to the accuracy requirements for a proper acetabulum reaming, removal of osteophytes, labrum, irregular bone and/or other unneeded tissue prior to reaming the acetabulum and during or after cup installation does not require a high degree of accuracy and could be quickly and easily completed by providing the surgeon with unrestricted control of the cutting tool. However, both actively and passively controlled systems do not provide the surgeon with this freedom from the surgical plan, and as a result, THAs and other types of actively or passively controlled surgical procedures take more time than necessary, thereby increasing operating room time.

Specifically, if a surgeon desires to follow an actively or passively controlled bone resection with a secondary manual resection to remove osteophytes, bone spurs, sharp edges, other non-uniformities and unnecessary tissue, the surgeon may need to first execute one or more of the following steps: (1) remove the robotic arm from the surgical site; (2) detach the cutting tool from the robotic arm for manual use; and/or (3) use a secondary manual cutting device. Any of these steps require additional time, costs and resources, including the use of additional anesthesia to complete the procedure. Further, the additional time required to complete the surgery increases the risk of vascular complications due to the use of tourniquets, increased risk of infection and other technical complications due to the use of additional devices and procedural steps. These additional steps also increase costs, use of operating room time and limit or prevent the surgeon from using his/her talents to perform corrective manual cutting during the robotic cutting process.

Therefore, there is a need for actively and/or passively controlled surgical robotic systems that can be used to perform constrained procedures that require a high degree of accuracy and related unconstrained procedures that do not require a high degree of accuracy in a more time efficient manner. While an orthopedic surgery is used as an example, this need exists for many other procedures, including other orthopedic procedures and non-orthopedic procedures.

SUMMARY OF THE DISCLOSURE

A surgical robotic system is disclosed for modifying a bone of a patient. The system includes a robotic arm and a surgical tool coupled to the robotic arm. A controller is programmed to be switchable between an at least partial manual control mode and an at least partial programmed control mode. In the at least partial programmed control mode, the controller is programmed to generate control signals that will limit movement or operation of the tool away from a programmed course to an intended location in or on the patient. Further, in the at least partial programmed mode, the controller is programmed to allow the tool to move and operate away from the programmed course without imposing resistance to movement or operation of the tool. In contrast, in the at least partial manual control mode, the controller is programmed to allow the tool to move and operate away from the programmed course without imposing resistance to movement or operation of the surgical tool.

A method for modifying a bone of a patient is also disclosed. The method includes registering a location of a planned modification of the bone with a surgical robotic system equipped with a controller programmed with an at least partial manual control mode and an at least partial programmed control mode. The system further includes a robotic arm and a surgical tool coupled to the robotic arm. The method also includes modifying the bone under the at least partial programmed control mode using the robotic arm and the tool. The method further includes deactivating the at least partial programmed control mode and activating the at least partial manual control mode. The method also includes resecting at least one of the tissue, osteophytes and irregular bone near the location of the modification of the bone in the at least partial manual control mode.

A surgical robotic system for performing hip arthroplasties is also disclosed. The system includes a robotic arm and a cutting tool coupled to the robotic arm. The system further includes a controller linked to the robotic arm and programmed to be switchable between an at least partial programmed control mode and an at least partial manual control mode. In the at least partial programmed control mode, the controller is programmed to compare an intended indentation in an acetabulum and a position of the cutting tool. The controller is also programmed to generate a course through which the controller allows the cutting tool to move without resistance and, the controller is programmed to impose resistance to movement of the tool away from the course. In the at least partial manual control mode, the controller is programmed to allow the cutting tool to operate away from the course without imposing resistance to movement of the cutting tool.

A method for resecting an acetabulum, osteophytes, irregular bone growth and soft tissue surrounding the acetabulum of a patient is also disclosed. The method includes registering a location of a planned resection of the acetabulum with a surgical robotic system including a controller programmed with an at least partial programmed control mode selected from the group consisting of a haptic control mode, an active control mode and a combination thereof. The controller is also programmed with a manual control mode. The system also includes a robotic arm and a reamer coupled to the robotic arm. The method includes turning off the at least partial programmed control mode and turning on the manual control mode. The method also includes resecting at least one of osteophytes, irregular bone growth and soft tissue that at least partially surround the acetabulum in the manual control mode, turning on the at least partial programmed control mode, and resecting the acetabulum under the at least partial programmed control mode using the robotic arm and the reamer.

Other advantages and features will be apparent from the following detailed description when read in conjunction with the attached drawings.

DETAILED DESCRIPTION OF THE PRESENTLY PREFERRED EMBODIMENTS

Surgical robotic systems are used in many types of surgery, including bone preparation for joint restorations, such as artificial and natural replacements, joint resurfacing of knees, shoulders, elbows, hips, wrists, spines, jaws, etc. Surgical robotic systems are also used for revisions of previous interventions, preparations and placements of temporary or permanent structures such as pins, anchors, rods, plates and other types of fixations. While the primary example disclosed in FIGS. 1-7 is directed toward a total hip arthroplasty, the systems and methods disclosed herein are applicable to bone preparations for joint restorations in general, skeletal corrections, corrective bone applications, osteotomies, revisions of previous interventions, preparation and placement of temporary structures, preparation in placement of permanent structures and combinations thereof.

Figure 1:
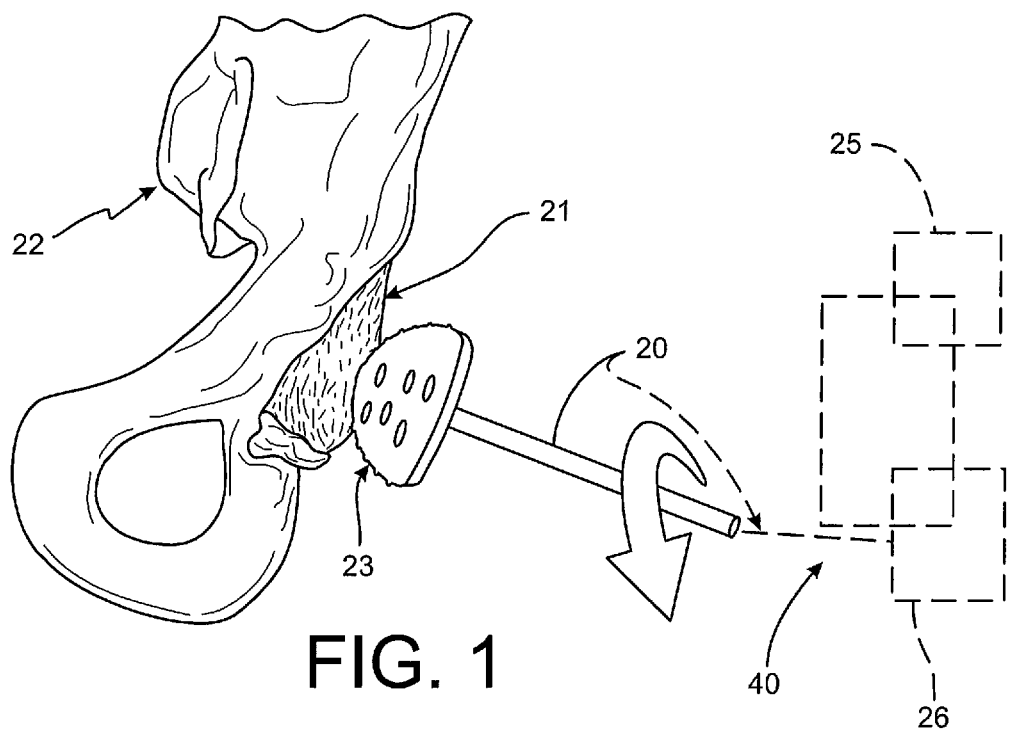
FIG. 1 is a perspective view of a reamer mounted on a robotic arm and engaging an acetabulum of a pelvis.

Turning to FIG. 1, a robotic arm is shown schematically at 20 and is coupled to a surgical tool 23, in this example, a semi-spherical reamer 23. The reamer 23 is shown engaging an acetabulum 21 which needs to be reamed so it may receive a semi-spherical acetabular cup (not shown) that, in turn, receives a resurfaced femoral head in a partial hip arthroplasty or, in the case of a total hip arthroplasty (THA), a ball portion of a hip implant (not shown).

Figure 2:
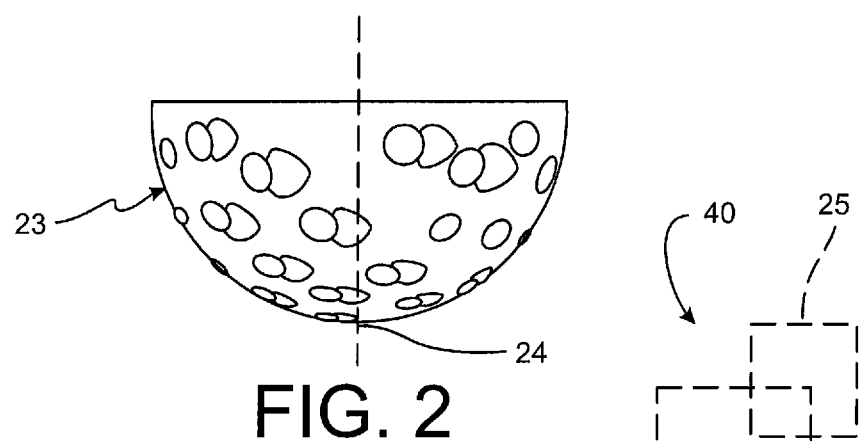
FIG. 2 is a plan view of a semi-spherical reamer.

The reaming of the acetabulum 21 is a procedure that requires a high degree of accuracy. Specifically, the accuracy of the location of the tool center point 24 of the reamer 23 as shown in FIG. 2 during a THA procedure is critical during the final bone preparation. Specifically, angular orientation of both the reamed socket and the implanted acetabular cup is important because incorrect orientation can result in misalignment of the acetabular cup away from the appropriate version and inclination angles of the acetabular anatomy. Misalignment can lead to post-operative problems, including joint dislocation, impingement of the femur on the acetabular cup at extreme ranges of motion, and accelerated wear of the acetabular cup due to improper loading of the femoral head-to-acetabular cup interface. Alignment is also important to maintain correct leg length and correct medial/lateral offset. Even more problematic, recent advances in THA reveal that the ideal acetabular cup position is in a narrower range than previously appreciated and that the acetabular cup position is dependant on the femoral component anteversion.

Figure 3:
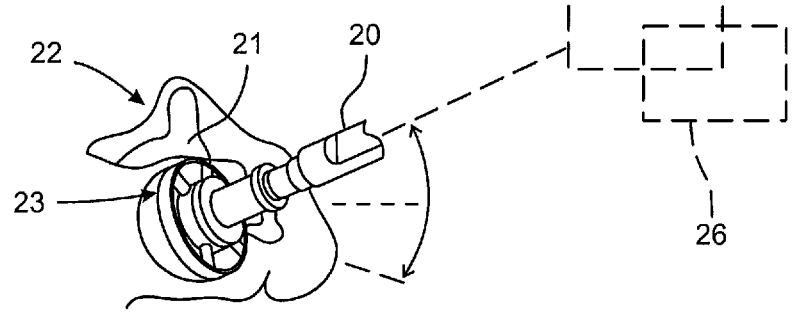
FIG. 3 is another perspective view of a reamer mounted on a robotic arm and engaging an acetabulum of a pelvis during the reaming of a semi-spherical indentation in the acetabulum.

Therefore, controlling the robotic arm 20 using a controller 25, as shown schematically in FIGS. 1 and 3, may be advantageous. Also shown schematically in FIGS. 1 and 3 is a handle 26 which may be used to control the robotic arm 20 in a manual or a partially manual manner. The handle 26 may be coupled directly or indirectly to the robotic arm 20. The handle 26 may take the arm of a joystick or end effector as disclosed in U.S. Patent Publication Nos. 2011/0082587, 2011/0082468 and 2011/0082462, which are commonly assigned with the present application.

When a high degree of accuracy is required, the controller 25 may be programmed to impose limitations on the movement of the reamer 23 and/or robotic arm 20 thereby making it difficult and/or time consuming for surgeons to complete some of the resections that do not require a high degree of accuracy. Specifically, the controller 25 may be programmed to impose passive (e.g. haptic) control or active (e.g. autonomous) control. U.S. Patent Application Publication Nos. 2006/0142657, 2001/0082587 and 2011/0082468 all discuss passively constrained haptic control for surgical robotic systems. Examples of actively constrained autonomous surgical robotic systems are disclosed in U.S. Pat. Nos. 7,492,116 and 6,162,171. A passively constrained haptic surgical robotic system is not intended to move autonomously on its own. In contrast, an actively constrained autonomous surgical robotic system that can be used for orthopedic joint replacement procedures is designed to perform bone cutting autonomously. Although the surgeon monitors the progress of the surgical tool or robot, and may interrupt the robot if necessary, the surgeon is not in full control of the procedure. An actively controlled surgical robotic system effectively takes the cutting instrument out of the surgeon's hands.

Figure 4:
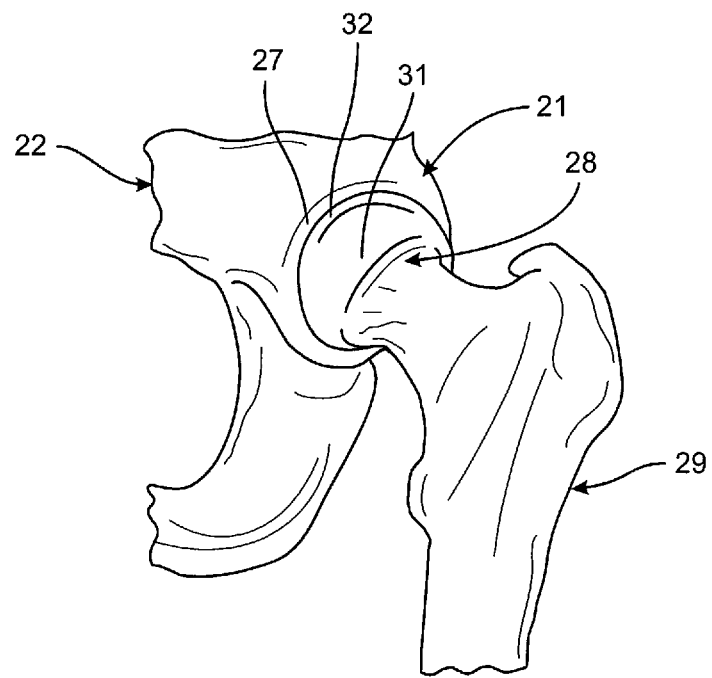
FIG. 4 illustrates a healthy hip joint including a portion of a pelvis, the acetabulum of the pelvis, the femur and the femoral head of the femur disposed in the acetabulum.
Figure 5:
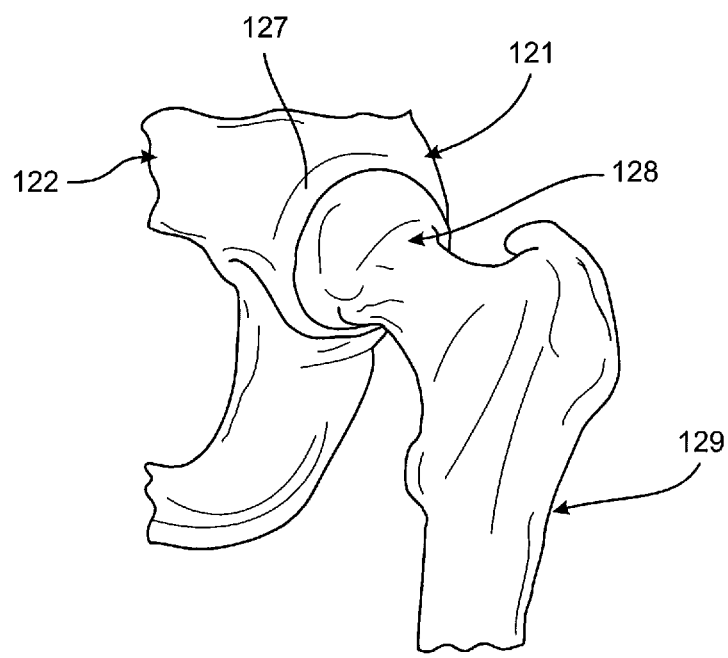
FIG. 5 illustrates another hip joint, as shown in FIG. 4, but with worn cartilage disposed on the femoral head and irregular bone in the form of rough bone, bone spurs and osteophytes surrounding the acetabulum.

Regardless of whether passive or active control is imposed by the controller 25 on movement of the surgical arm 20 and surgical tool 23, one disadvantage of both types of control systems is illustrated in FIGS. 4-5. Specifically, FIG. 4 illustrates a healthy hip joint that includes a pelvis 22, acetabulum 20, acetabular rim 27, femoral head 28 and femur 29. The femoral head 28 is covered with smooth cartilage 31 that engages the labrum 32 that provides smooth weight bearing surfaces. In contrast, a diseased hip joint is illustrated in FIG. 5 that also includes a pelvis 122 in an acetabulum 121. The acetabular rim 127 is covered by osteophytes, rough bone, bone spurs and other bone irregularities that restrict access of the reamer 23 (see FIGS. 1-3) to the acetabulum 121. The femoral head 128 is also covered by worn cartilage. To provide better access to the acetabulum 121, the surgeon may want to remove the irregular bone from the acetabular rim 127 and also remove any unnecessary tissue that may restrict access to the acetabulum 121. The resection of the irregular bone surrounding the acetabulum 121 or on the acetabular rim 127 as well as the resection of unnecessary tissue does not require a high degree of precision and can be most sufficiently performed by a surgeon free handed. To take advantage of this sufficiency, the disclosed systems and methods provide an easy means for turning on and turning off the control system, whether it be passive or active control.

Figure 6:
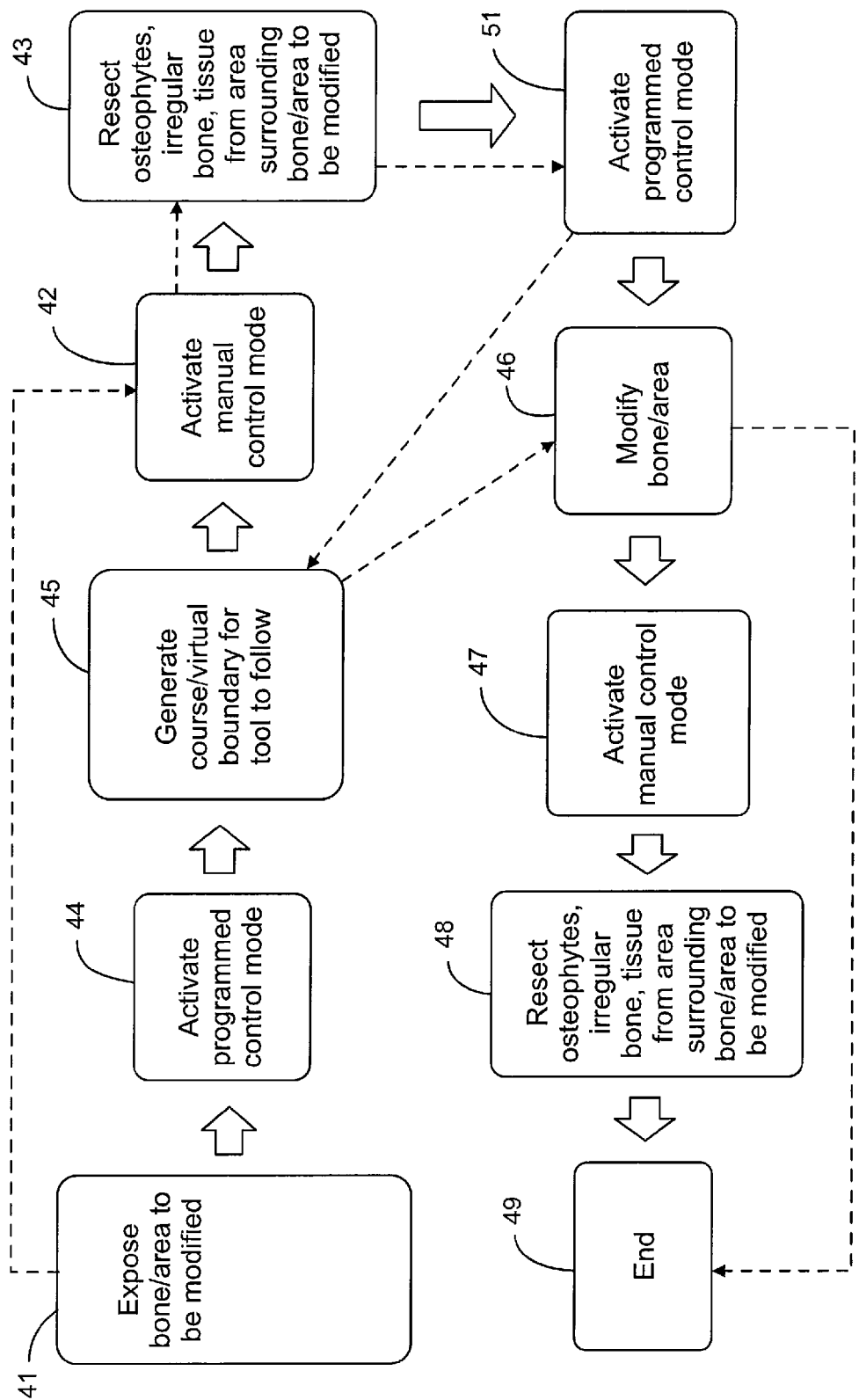
FIG. 6 is a flow diagram illustrating various disclosed methods for modifying a bone of a patient using the disclosed systems and methods.
Figure 7:
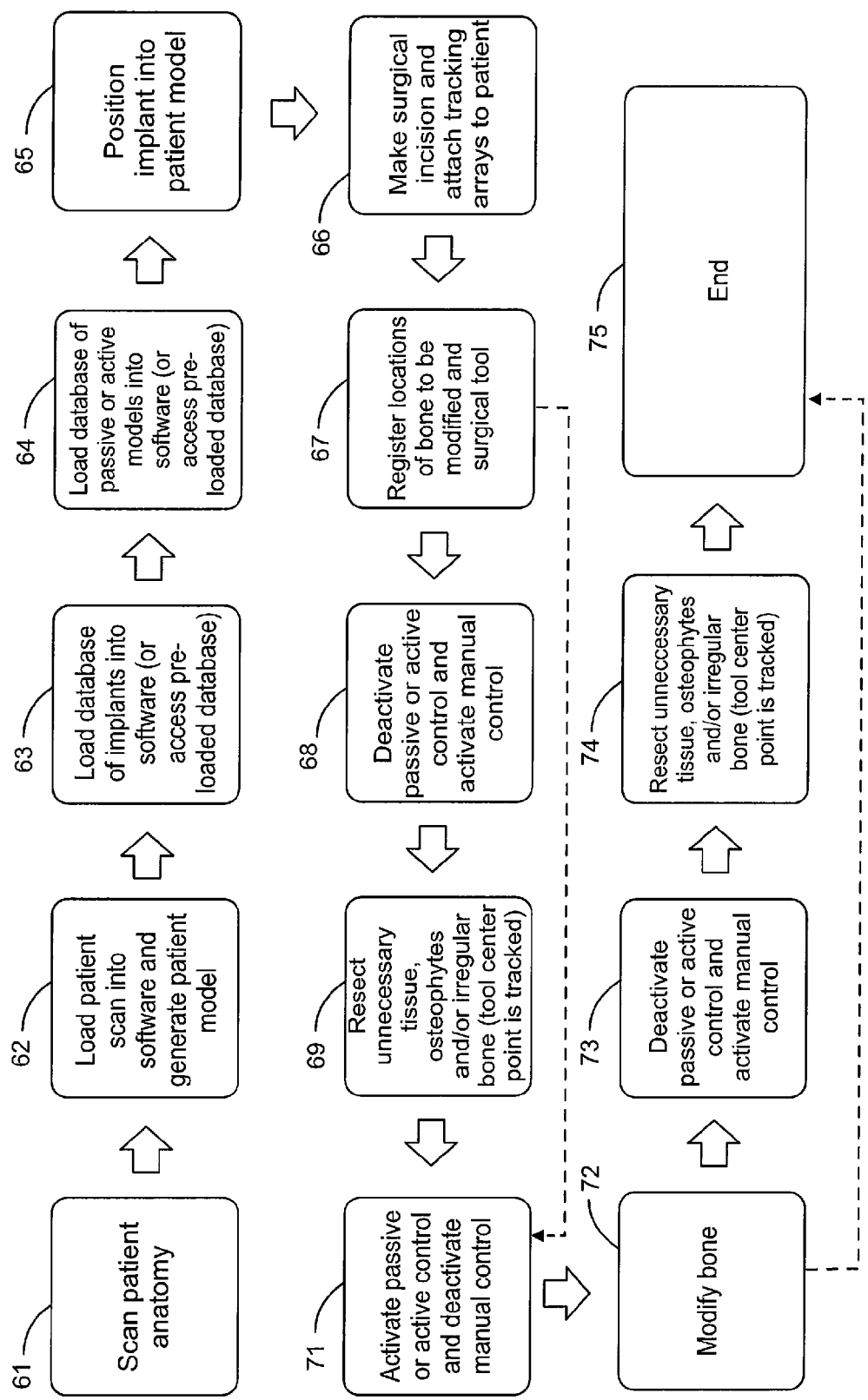
FIG. 7 is another flow diagram illustrating various disclosed methods for modifying a bone of a patient using the disclosed systems or methods.

Turning to FIG. 6, one method of employing the disclosed surgical robotic system 40 is illustrated in FIGS. 1 and 3. First, at step 41, the surgeon makes an incision in the patient to expose the bone or area that is to be modified. The preliminary steps before the incision is made are illustrated in FIG. 7 and will be discussed below. After the incision is made, the surgeon has the option of activating a manual control mode at step 42 for the purpose of resecting any osteophytes, irregular bone, or tissue from the area surrounding the bone or area to be modified at step 43. Otherwise, the programmed control mode, either passive or active, can be activated at step 44 and the controller 25 (FIGS. 1 and 3) will generate a course, path or virtual boundary for the surgical tool 23 (FIGS. 1 and 3) to follow at step 45. After the course, path or virtual boundary is defined by the controller 25 at step 45, the surgeon may elect to activate the manual control mode at step 42 and resect any osteophytes, irregular bone, or tissue from the area surrounding the bone or area to be modified at step 43 prior to the commencement of bone removal using the haptic or passive control modes at steps 51 and 46. Further, after the course, path or virtual boundary for the tool to follow is defined at step 45, the surgeon may go ahead and modify the bone or area at step 46 prior to any manual resections of bone or tissue at step 43. After the bone or area is modified at step 46, the manual control may be activated at step 47 and a manual resection is carried out at step 48 prior to conclusion of the procedure at step 49. If a manual resection is done at step 43 prior to modification of the bone or area at step 46, the system must be switched back to programmed control mode, either passive or active control, at step 51.

Thus, the manual resections may be carried out before the computer assisted procedure at step 46 as shown by the manual resections at step 43 (before the computer assisted resection at step 46) or at step 48 (after the computer assisted resection at step 46). Further, it is possible that the programmed (active and/or passive) and manual control modes are operating simultaneously. It is also possible that the active or passive control mode may still be "on", but any tactile resistance capabilities are shut off while the controller 25 is operating in a manual or at least partially manual control mode. This may enable operation of the robotic arm 20 and surgical tool 23 in the manual control mode to be tracked using the navigational capabilities of the controller 25.

Turning to FIG. 7, the disclosed methods are illustrated in greater detail. Initially, a patient is scanned at step 61 and the patient scan is loaded into the software of the controller 25 and a model is generated by the controller 25 at step 62. Optionally, a database of implants may be loaded into the software at step 63 or the database of implants may be pre-loaded into the database. Similarly, at step 64, a database of passive or active control models may be loaded into the software of the controller 25 or such models may be pre-loaded. At step 65, the implant or bone modification may be positioned in the patient model generated at step 62. Then, at step 66, a surgical incision may be made to expose the bone or area to be modified and tracking arrays are attached to the patient as would be apparent to those skilled in the art. Locations of the patient's bone that needs modification as well as the surgical tool 23 at the end of the robotic arm 20 are registered with the software of the controller 25 at step 67. Then, the manual control may be activated at step 68 and manual resections may be carried out at step 69. In contrast, after registration takes place at step 67, the active or passive control may be maintained or activated at step 71 and the primary procedure may be carried out at step 72. Then, the active or passive control may be deactivated at step 73 thereby activating manual control and manual resections may be carried out at step 74 to conclude the procedure at step 75. Thus, manual resections may be carried out before or after the computer assisted procedure which may be carried out under a passive or active control scheme.

It will be noted that both soft tissue and bone can be removed manually without the need for passive or active control of the cutting tool 23. It will be also noted that both bone modification as well as hard tissue modification may be carried out using the passive or active control schemes. In the THA procedure illustrated in FIGS. 1-5, the active or passive control schemes are able to provide proper alignment of the acetabular cup as well as precise preparation of the implant socket disposed in the acetabulum 21. Preferably, the activation or deactivation or the turning on and off of the passive or active control schemes is a button selection in the software. However, a hardware switch may be employed as well.

INDUSTRIAL APPLICABILITY

Interactive and autonomous robotic systems are used for many types of surgeries. However, a common method of removing tissue such as osteophytes, irregular bone growths, bone spurs and unnecessary tissue is to use a manually controlled, motorized cutting device, such as a saw, drill, burr or reamer. In a more traditional passively constrained haptic system, the surgical navigation aspect of the haptic system assists the surgeon's manual use of the cutting tool with visual guidance and a mechanically constrained method to maintain the cutting device on a planned path, course, trajectory, plane and/or depth. However, in both passively and actively controlled surgical robotic systems, the surgeon does not have unconstrained use of the cutting tool and typically cannot execute the needed bone resections around an acetabular rim 27 or tissue removal surrounding an acetabulum 21 as such resections will not generally be disposed along the desired trajectory for reaming.

Thus, actively controlled orthopedic robots take the cutting tool out of the hands of the surgeons and passively controlled orthopedic robots limit the use of the cutting tool by a surgeon. In the past, a surgeon would generally have to follow a resection strictly limited by a surgical plan with a secondary manual resection to remove the osteophytes, irregular bone spurs, sharp edges and other non-uniformities that may have been created during the primary cutting or reaming process. The additional manual resection is common during the process of fitting an implant to a bone surface. For a surgeon to complete these additional manual resection steps, the surgeon may need to remove the robot from the surgical site, detach the cutting tool from the robot for manual use and/or use a secondary manual cutting device. Any or all of these options require additional time and resources to complete the procedure. They also limit the ability of the surgeon to perform corrective manual cutting during the robotic process. However, the methods illustrated in FIGS. 6-7 overcome these disadvantages by enabling the surgeon to use the primary cutting tool (see the reamer 23 in FIGS. 1 and 3) to manually remove boney growths or unnecessary tissue.

There are significant benefits by selectively allowing the same cutting tool 23 to be (1) actively controlled by the robot, and/or (2) manually controlled by the surgeon while passively guided or constrained by the robot and (3) manually and freely controlled by the surgeon without the need to remove the robot from the surgical site for the purposes of detaching components or to require a secondary cutting system to complete the procedure.

In essence, giving surgeon the ability to move back and forth between passive or active control and a manual control can improve the patients outcomes and safety by reducing complications that occur in proportion to the duration of a surgical procedure which include, but are not limited to (1) a reduced use of anesthesia, (2) reduced vascular complications due to the use of a tourniquet, (3) reduced risk of infection associated with the reduced length of the procedure and reduced number of surgical tools employed and (4) reduced technical complications due to fewer devices and procedural steps. The disclosed methods and systems may also reduce procedural costs by (1) making the procedures faster, thereby utilizing yet less operating room time, (2) reducing the number of tools used and disposable items required per procedure, and (3) reducing capital costs associated with using fewer surgical devices.

The invention claimed is:

1. A surgical robotic system for modifying, a bone of a patient, the system comprising:
a robotic arm;
a tool coupled to the robotic arm; and
a controller programmed to be switchable between an at least partial manual control mode and an at least partial programmed control mode;
in the at least partial programmed control mode, the controller is programmed to generate control signals that will limit movement or operation of the tool away from a programmed course;
in the at least partial manual control mode, the controller is programmed to allow the tool to move and operate away from the programmed course without imposing resistance to movement or operation of the tool; and
wherein the tool is selected from the group consisting of reamers, saws, chills, burrs and combinations thereof.

2. The system of claim 1 wherein the at least partial programmed control mode is selected from the group consisting of passive control, active control, and combinations thereof.

3. The system of claim 1 wherein the at least partially manual control provides unrestricted freedom to move and operate the tool.

4. The system of claim 1, wherein the at least partial programmed control mode is a haptic control mode and the programmed course is a virtual cutting boundary, wherein, in the haptic control mode, the controller is programmed to:
compare an intended modification to the bone and a position of the tool; and
generate control signals that will at least assist in directing the tool along or within the virtual cutting boundary and constrain movement of the tool away or outside of the virtual cutting boundary.

5. The system of claim 1 wherein movement of the robotic arm in the at least partial manual control mode is performed using a joystick.

6. The system of claim 1 wherein, in the at least partial programmed control mode, movement of the robotic arm by a surgeon is performed using a joystick, and any resistance to movement or operation of the tool away from the programmed course is provided through the joystick.

7. The system of claim 1 wherein the programmed course is a virtual cutting boundary that is selected from the group consisting of a haptic volume, a haptic path, a planned trajectory, a planned plane and a planned depth.

8. The system of claim 1 wherein the controller is further programmed to allow limitless switching between the at least partial manual control mode and the at least partial programmed control mode.

9. The system of claim 1 wherein both the at least partial manual control mode and the at least partial programmed control mode includes use of an image of the patient's anatomy for navigational purposes.

10. The system of claim 9 wherein the controller is further programmed to track at least a portion of a tool and display the portion of the tool on the image of the patient.

11. A method for modifying a bone of a patient, the method comprising:
- registering a location of a planned modification of the bone with a surgical robotic system equipped with a controller programmed with an at least partial manual control mode and an at least partial programmed control mode, the system further including a robotic arm and a tool coupled to the robotic arm;
- modifying the bone under the at least partial programmed control mode using the robotic arm and the tool;
- deactivating the at least partial programmed control mode and activating the at least partial manual control mode; and
- resecting at least one of tissue, osteophytes and irregular bone near the location of the modification of the bone in the at least partial manual control mode;
- wherein the modifying of the hone is selected from the group consisting of bone preparation for joint restorations, skeletal corrections, corrective bone applications, osteotomies, revisions of previous interventions, preparation and placement of temporary structures, preparation and placement of permanent structures and combinations thereof.

12. The method of claim 11 wherein the resecting of at least one of tissue, osteophytes and irregular bone is performed before or after the modifying of the bone.

13. The method of claim 11 wherein the modifying of the bone and the resecting of at least one of tissue, osteophytes and irregular bone is performed at least in part using a joystick.

14. The method of claim 11 wherein the resecting at least one of tissue, osteophytes and irregular bone near the location of the modification of the bone is carried out multiple times and before or after the modification of the bone.

15. The method of claim 11 wherein the at least partial programmed control mode is selected from the group consisting of haptic control, active control, haptic control using a joystick and combinations thereof.

16. The method of claim 11 wherein the at least partial programmed control mode is a haptic control mode, and in the haptic control mode, the method further including:
- comparing an intended modification to the hone and a position of the tool;
- generating a virtual cutting boundary; and
- generating control signals that will at least assist in moving the tool along or within the virtual cutting boundary and constraining movement of the tool away or outside of the virtual cutting boundary.

17. The method of claim 16 wherein the moving of the tool along or within the virtual cutting boundary is carried out using a joystick and the constraining of movement of the tool is felt through the joystick.

18. The method of claim 11 wherein both the at least partial manual control mode and the at least partial programmed control mode includes use of an image of the patient for navigational purposes.

19. The method of claim 18 wherein the controller is thither programmed to track a portion of a tool and display the portion of the tool on the image in both the at least partial manual control mode and the at least partial programmed control mode.

20. A surgical robotic system for modifying a bone of a patient, the system comprising:
- a robotic arm;
- a tool coupled to the robotic arm; and
- a controller programmed to be switchable between an at least partial manual control mode and an at least partial programmed control mode;
- in the at least partial programmed control mode, the controller is programmed to generate control signals that will limit movement or operation of the tool away from a programmed course;
- in the at least partial manual control mode, the controller is programmed to allow the tool to move and operate away from the programmed course without imposing resistance to movement or operation of the tool; and
- wherein the programmed course is a virtual cutting boundary that is selected from the group consisting of a haptic volume, a haptic path, a planned trajectory, a planned plane and a planned depth.

21. The system of claim 20 wherein the at least partial programmed control mode is selected from the group consisting of passive control, active control, and combinations thereof.

22. The system of claim 20 wherein the at least partially manual control provides unrestricted freedom to move and operate the tool.

23. The system of claim 20 wherein the at least partial programmed control mode is a haptic control mode and the programmed course is a virtual cutting boundary, wherein, in the haptic control mode, the controller is programmed to:
- compare an intended modification to the bone and a position of the tool; and
- generate control signals that will at least assist in directing the tool along or within the virtual cutting boundary and constrain movement of the tool away or outside of the virtual cutting boundary.

24. The system of claim 20 wherein movement of the robotic arm in the at least partial manual control mode is performed using a joystick.

25. The system of claim 20 wherein, in the at least partial programmed control mode, movement of the robotic arm by a surgeon is performed using a joystick, and any resistance to movement or operation of the tool away from the programmed course is provided through the joystick.

* * * * *

UNITED STATES PATENT AND TRADEMARK OFFICE
CERTIFICATE OF CORRECTION

PATENT NO.         : 8,498,744 B2
APPLICATION NO.    : 13/174051
DATED              : July 30, 2013
INVENTOR(S)        : Daniel Odermatt et al.

It is certified that error appears in the above-identified patent and that said Letters Patent is hereby corrected as shown below:

In The Claims

On column 8, line 28: please replace "chills" with -- drills --

On column 9, line 17: please replace "hone" with -- bone --

Signed and Sealed this
Twenty-eighth Day of June, 2016

Michelle K. Lee
*Director of the United States Patent and Trademark Office*